US006392084B1

(12) United States Patent
Kaieda et al.

(10) Patent No.: US 6,392,084 B1
(45) Date of Patent: May 21, 2002

(54) METHOD FOR PRODUCTION OF ORGANIC FLUORINE COMPOUND

(75) Inventors: Osamu Kaieda, Tsuchiura; Koichi Hirota, Kobe, both of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/139,192

(22) Filed: Aug. 25, 1998

(30) Foreign Application Priority Data

Aug. 26, 1997 (JP) ............................................. 9-229615

(51) Int. Cl.[7] ........................ C07C 255/50; C07C 63/10
(52) U.S. Cl. ........................ 558/425; 562/493; 558/411
(58) Field of Search ................................. 562/103, 493; 558/411, 425; 546/345

(56) References Cited

U.S. PATENT DOCUMENTS 4,684,734 A * 8/1987 Kaieda et al. ............... 546/345
4,978,769 A * 12/1990 Kysela et al. ............... 558/423

FOREIGN PATENT DOCUMENTS

EP     0 354 444 A2 *  8/1989 ........... C07C/17/20

OTHER PUBLICATIONS

Lewis, Hawley's Condensed Chemical Dictionary, twelfth edition, pp. 950, 954, 1058, 1059, 1062, 1993 No month provided.*

Aldrich Catalog Handbook of Fine Chemicals, pp. 144 and 1250, 1996–1997.*

Ishikawa, "Fluorination of Aromatic Compounds by Halogen Exchange", Journal of Organic Synthetic Chemical Society, 25:808, 1976 No month provided.*

Ueda et al., "A New Route to Tetrafluorophthalonitrile and Tetrafluoroterephthalonitrile", Bull. Chem. Soc. 40(3):688–689, 1967 No month provided.*

Chemistry of Organic Fluorine Compounds pp. 112–137, 1967 No month provided.*

* cited by examiner

*Primary Examiner*—Deborah D. Carr
*Assistant Examiner*—Rosalynd Keys
(74) *Attorney, Agent, or Firm*—Fish & Richardson P.C.

(57) ABSTRACT

A method for the production of an aromatic fluorine compound is provided which is capable of preventing the occurrence of benzoic acid fluorides during the course of a halogenation exchange reaction or allowing removal of the benzoic acid fluorides formed at all. A method for the production of an organic fluorine compound is disclosed which comprises preventing the occurrence of acid fluorides of an aromatic compound during the production of the organic fluorine compound by the reaction of an organic chlorine or bromine compound with a fluorinating agent in benzonitrile as a solvent or allowing removal of the acid fluorides formed.

17 Claims, 1 Drawing Sheet

METHOD FOR PRODUCTION OF ORGANIC FLUORINE COMPOUND

BACKGROUND OF THE INVENTION

1. Field of the Invention

This invention relates to a method for the production of an organic fluorine compound. More particularly, it relates to an improvement in a method for the production of an organic fluorine compound by a so-called halogenation exchange reaction, i.e. the reaction of an organic chlorine or bromine compound with a fluorinating agent in benzonitrile as a solvent.

2. Description of the Related Art

The so-called halogen exchange reaction which comprises exchanging a halogen atom for a fluorine atom by the action of an alkali fluoride on an aromatic halide has been known for a long time. Generally as the solvent for this reaction, such so-called aprotic polar solvents as dimethyl sulfoxide (DMSO), sulfolane (TMSO$_2$), N-dimethyl formamide (DMF), N-methyl-2-pyrrolidone (NMP), and dimethyl sulfone (DMSO$_2$) have been mainly used. The halogenation exchange reaction, therefore, is carried out at a temperature not higher than the boiling point of the relevant solvent [Ishikawa, Journal of Organic Synthetic Chemical Society, Vol. 25, page 808 (1967), M. Hudlicky, Chemistry of Organic Fluorine Compounds, page 112 (1976), John Wiley & Sons Press, etc. refer, for example]. Cases of the reaction incorporating such an interphase transfer catalyst as a crown compound in the reaction system for the purpose of accelerating the reaction velocity have been reported.

When the halogen exchange reaction is performed by the method described above, however, the halogen of an aromatic monohalide and an aromatic polyhalide having a halogen substituent at the ortho or para position of the electron attractive group (such as, for example, —CN and —NO$_2$) easily succumbs to halogen exchange but the halogen at the meta position does not easily succumb to halogen exchange.

The solvents in popular use, when heated to an elevated temperature or kept heated for a protracted duration for the purpose of improving yields, undergo a decomposition reaction or induce a secondary reaction with a raw material or with the product of reaction and eventually fail to improve the yield. Further, in the recovery or reclamation of the solvents after use, these solvents are at a disadvantage in not allowing easy commercial use of recovered or reclaimed solvents. With a view to overcoming the drawback of these solvents being unusable at elevated temperatures, the method which carries out the reaction in an autoclave at a high temperature in the range of 200°–500° C. without use of a solvent has found popular acceptance. The case of effecting halogenation exchange of tetrachlorophthalonitrile for tetrafluoroterephthalonitrile in an autoclave at a temperature of 300° C. without use of a solvent has been reported, for example, in Ueda et al., Bull. Chem. Soc. Japan, Vol. 40, page 638. Since this method uses no solvent, the reaction which is exothermic in form allows no easy temperature control and the reaction, when completed, suffers a large volume of carbide to persist as a fast deposited residue on the inner wall of the reaction vessel. Thus, the method may well be regarded as a commercially impracticable approach.

As a means to solve this problem, we have disclosed in U.S. Pat. No. 4,684,734 a method for producing an organic fluorine compound by causing an organic chlorine or bromine compound to react with a fluorinating agent in benzonitrile as a solvent at a temperature in the range of 190°–400° C. under at least the spontaneously generated pressure. This method, while converting the organic chlorine or bromine compound through halogen exchange into a corresponding organic fluorine compound, enjoys thermal stability even at an elevated temperature because benzonitrile as a solvent is thermally stable and further avoids inducing such a secondary reaction with a raw material or the product of reaction as observed in the case of other solvents. Thus, the solvent ensures safety use at high temperatures in the range of 190°–400° C., allows the reaction temperature to be elevated as required, and contributes to the improvement of yields. It is also at an advantage in avoiding such a secondary reaction with a raw material or the product of reaction as encountered by other solvents. Owing to the use of this solvent, this method, unlike the method using no solvent, is at an advantage in allowing easy control of temperature and precluding the formation of a large amount of carbide. This method, when commercially used, has the advantage of forming the product aimed at in high yields.

This method of production, however, still has such problems as generating during the halogen exchange reaction acid fluorides of an aromatic compound in an amount in the approximate range of 1000–8000 ppm (as fluorine ion to be generated) based on the amount of the organic fluorine compound and exposing the plant facilities, during the halogen exchange reaction and at the subsequent step of production, to corrosion owing to the formation of hydrofluoric acid (fluorine ions), a corrosive substance originating in the acid fluorides of the relevant aromatic compound.

An object of this invention, therefore, is to provide a novel method for the production of an organic fluorine compound.

Another object of this invention is to provide a method for producing an organic fluorine compound by causing an organic chlorine or bromine compound to react with a fluorinating agent in benzonitrile as a solvent, which method is capable of preventing the occurrence of a benzoic acid fluoride during the halogenation exchange reaction.

Still another object of this invention is to provide a method for producing an organic fluorine compound by causing an organic chlorine or bromine compound to react with a fluorinating agent in benzonitrile as a solvent, which method is capable of removing the benzoic acid fluoride generated during the halogenation exchange reaction.

SUMMARY OF THE INVENTION

We have made a diligent study in search of a novel method for producing an organic fluorine compound with a view to accomplishing the objects mentioned above. We have perfected this invention as a result.

Specifically, the objects of this invention mentioned above are accomplished by (1) a method for producing an organic fluorine compound which comprises causing an organic chlorine or bromine compound to react with a fluorinating agent in benzonitrile as a solvent in the presence of the oxide, hydroxide, and/or carbonate of an alkali metal or alkaline earth metal under preventing the occurrence of acid fluorides of an aromatic compound or effecting removal of acid fluorides of the aromatic compound formed.

The objects of this invention mentioned above are further accomplished by (2) a method for the production of an organic fluorine compound, which comprises causing an organic chlorine or bromine compound to react with a fluorinating agent in benzonitrile as a solvent, treating the reaction solution or reaction product with an aqueous liquid, and then separating a water layer thereby removing acid fluorides of an aromatic compound.

The objects of this invention mentioned above are further accomplished by (3) a method set forth in (2) above, where in the aqueous liquid is an acidic aqueous liquid.

The objects of this invention mentioned above are further accomplished by (4) a method set forth in (2) or (3) above, wherein the reaction is carried out in the presence of oxide, hydroxide, and/or carbonate of an alkali metal or alkaline earth metal.

The objects of this invention mentioned above are further accomplished by (5) a method set forth in any of (1)–(4) above, wherein the organic chlorine or bromine compound is a chloride or bromide aromatic compound.

The objects of this invention mentioned above are further accomplished by (6) a method set forth in any of (1)–(5) above, wherein the fluorinating agent is at least one member selected from the group consisting of fluorides of alkali metal and alkaline earth metals.

The methods of this invention mentioned above are further accomplished by (7) a method set forth in any of (1)–(6) above, wherein the acid fluoride of an aromatic compound is benzoic acid fluoride.

The objects of this invention mentioned above are further accomplished by (8) a method set forth in any of (1)–(7) above, wherein the organic chlorine or bromine compound is pentachlorobenzonitrile and the organic fluorine compound is pentafluorobenzonitrile.

The objects of this invention mentioned above are further accomplished by (9) a method for the production of pentafluorobenzoic acid, which comprises causing pentachlorobenzonitrile to react with a fluorinating agent in benzonitrile as a solvent thereby obtaining pentafluorobenzonitrile, hydrolyzing the benzoic acid fluoride present in the resultant reaction solution with an acidic aqueous liquid and inducing separation of the hydrolyzate on the water layer side, and then hydrolyzing the pentafluorobenzonitrile resulting from the treatment in an aqueous sulfuric acid solution thereby producing the pentafluorobenzoic acid.

By this invention, the corrosion possibly caused during the process of halogen exchange reaction can be prevented.

This invention can further prevent the occurrence of fluorine ions, a corrosive substance, during the process of hydrolysis which follow the process of halogen exchange reaction.

DESCRIPTION OF THE PREFERRED EMBODIMENT

Figure 1:
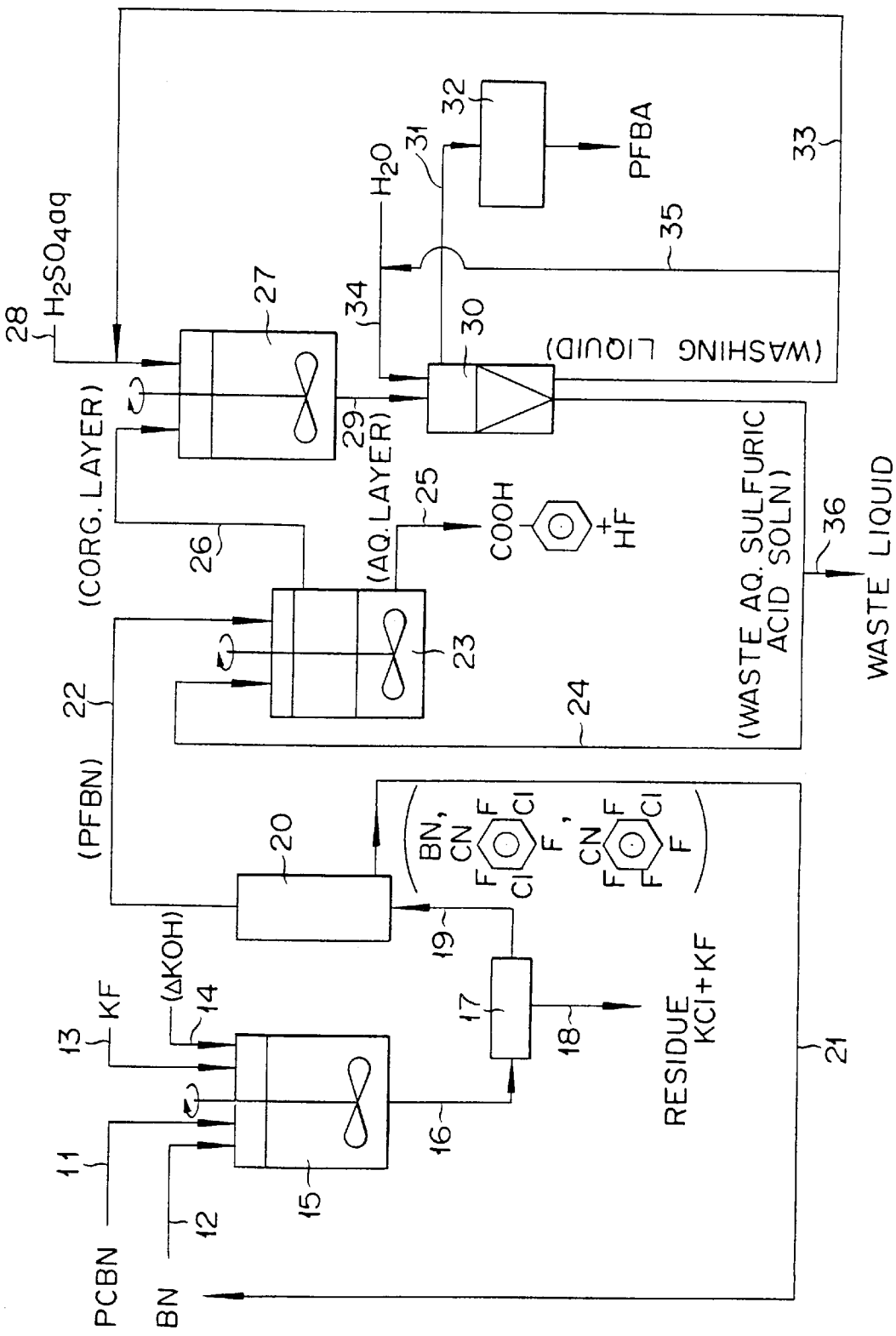
FIG. 1 is a schematic diagram illustrating one preferred embodiment of a device for production to be used in the method of this invention for the production of pentafluorobenzoic acid.

The method of this invention for the production of an organic fluorine compound is characterized by preventing the formation of acid fluorides of an aromatic compound during the production of the organic fluorine compound by the reaction of an organic chlorine or bromine compound with a fluorinating agent in benzonitrile as a solvent or removing the acid fluorides suffered to occur at all. The fact that the formation of acid fluorides of the aromatic compound is prevented or the acid fluorides suffered to form at all are removed can manifest an effect of preventing the reaction vessel from corrosion during the process of halogen exchange reaction and preventing the occurrence of fluorine ions, a corrosive substance, while the produced organic fluorine compound is subjected as an intermediate to such further reactions as hydrolysis.

One of the methods for the production of an organic fluorine compound as a means for accomplishing the objects of this invention is characterized by causing the reaction of an organic chlorine or bromine compound with a fluorinating agent in benzonitrile as a solvent to proceed in the presence of the oxide, hydroxide, and/or carbonate of an alkali metal or alkaline earth metal. The presence of the oxide, hydroxide, and/or carbonate of an alkali metal or alkaline earth metal at the site of the reaction can manifest an effect of preventing the occurrence of acid fluorides of an aromatic compound during the process of the halogen exchange reaction.

It is inferred that the acid fluorides of an aromatic compound are formed by the following mechanism in the case of benzoic acid fluoride, for example.

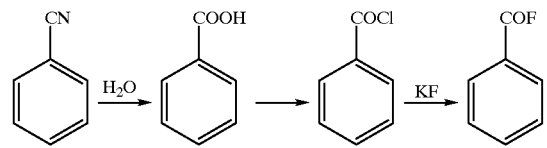

This mechanism is inferred to comprise forming benzoic acid by the reaction of the water contained in a minute amount (about 500–1,000 ppm) in the reaction solution with the benzonitrile solvent, converting the benzoic acid into benzoic acid chloride (benzoyl chloride) through substitution with chlorine ions also contained in the reaction solution, and converting the benzoic acid chloride into benzoic acid fluoride (benzoyl fluoride) through substitution with a fluorinating agent (such as, for example, potassium fluoride) (the amount of benzoic acid fluoride formed falling in the approximate range of 1,000–8,000 ppm) based on the amount of the organic fluorine compound obtained by the halogen exchange reaction.

We, based on the inference mentioned above, have discovered that the presence of the oxide, hydroxide, and/or carbonate product of an alkali metal or alkaline earth metal during the process of the halogenation exchange reaction can decompose the benzoic acid chloride and consequently prevent the formation of acid fluorides of the aromatic compound.

As typical examples of the oxide, hydroxide, and/or carbonation product of an alkali metal or alkaline earth metal, such oxides of alkali metals as $Na_2O$ and $K_2O$, such oxides of alkaline earth metals as $MgO$ and $CaO$, such hydroxides of alkali metals as $NaOH$ and $KOH$, such hydroxides of alkaline earth metals as $Mg(OH)_2$ and $Ca(OH)_2$, such carbonates of alkali metals as $Na_2CO_3$ and $K_2CO_3$, and such carbonation products of alkaline earth metals as $MgCO_3$ and $CaCO_3$ may be cited. Among other examples cited above, hydroxides of alkali metals are preferable and $KOH$ is particularly preferable on account of high effectiveness.

The amount of the oxide, hydroxide, and/or carbonate of an alkali metal or alkaline earth metal to be added is in the range of 50–1,500 ppm, preferably in the range of 100–600 ppm. If the amount so added is less than 50 ppm, the effect of preventing the formation of acid fluorides of an aromatic compound will not be sufficient. Conversely, if this amount exceeds 1,500 ppm, the excess will be at a disadvantage in causing the starting raw material to succumb easily to such secondary reactions as the reaction of hydroxylation.

The method of the present invention which is constructed as described above can repress the content of acid fluorides in the aromatic compound formed during the halogenation exchange reaction to a level of not more than about 2,000 ppm, based on the amount of the product. Owing to this fact, the reaction vessel made of stainless steel, for example, can be prevented from corrosion.

The acid fluorides of an aromatic compound which the present invention aims to prevent or remove even embrace those originating in trace impurities contained in the starting raw material besides benzoic acid fluoride. As typical examples of the acid fluorides originating in the impurities, tetrafluoro-benzoic acid fluoride, tetrachlorobenzoic acid fluoride, monochlorobenzoic acid fluoride, monofluorobenzoic acid fluoride, dichlorobenzoic acid fluoride, difluorobenzoic acid fluoride, tetrachlorophthalic acid fluoride, and tetrafluorophthalic acid fluoride may be cited.

As the organic chlorine or bromine compound which is the starting raw material compound in this invention, all the compounds that are possessed of at least one chlorine atom or bromine atom are invariably usable. Those compounds which have part of chlorine atoms or bromine atoms already substituted by fluorine are also usable. In these organic chlorine or bromine compounds, aromatic chloride or bromide compounds are preferable and aromatic chloride or bromide compounds represented by the following formula (1)

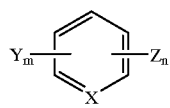

(1)

wherein X is N, CY, or CZ, Y is Cl or Br, Z is F, CN, or $NO_2$, m is an integer of 1–5, n is an integer of 0–4, and the sum of m and N is an integer of 1–5, are particularly preferable.

Further, in the aromatic chloride or bromide compounds represented by the formula (1) mentioned above, the aromatic chloride or bromide compounds represented by the formula (2)

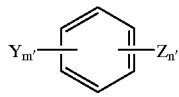

(2)

wherein Y is Cl or Br, Z is F, CN, or $NO_2$, m' is an integer of 1–6, n' is an integer of 0–5, and the sum of m' and n' is an integer of 1–6, or the formula (3)

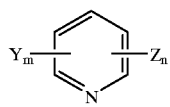

(3)

wherein Y is Cl or Br, Z is F, CN, or $NO_2$, m is an integer of 1–5, n is an integer of 0–4, and the sum of m and n is an integer of 1–5, are preferable.

In the aromatic chloride or bromide compounds represented by the formula (2) mentioned above, the aromatic chloride or bromide compounds represented by the formula (4)

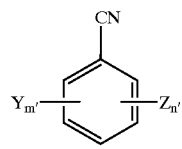

(4)

wherein Y is Cl or Br, m is an integer of 1–5, n is an integer of 0–4, and the sum of m and is an integer of 1–5, or the formula (5)

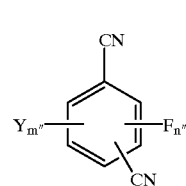

(5)

wherein Y is Cl or Br, m' is an integer of 1–4, n' is an integer of 0–3, and the sum of m' and n' is an integer of 1–4, are particularly preferable.

In the aromatic chloride or bromide compounds represented by the formula (3) mentioned above, the aromatic chloride or bromide compounds represented by the formula (6)

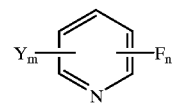

(6)

wherein Y is Cl or Br, m is an integer of 1–5, n is an integer of 0–4, and the sum of m and n is an integer of 1–5, or the formula (7)

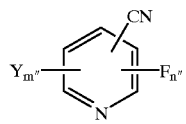

(7)

wherein Y is Cl or Br, m" is an integer of 1–4, n" is an integer of 0–3, and the sum of m" and n" is an integer of 1–4, are particularly preferable.

As typical examples of the chloride or bromide aromatic compound, chlorobenzene, polychlorobenzenes, o-chloronitrobenzene, m-chloronitrobenzene, p-chloronitrobenzene, 2,4-dinitrochlorobenzene, o-chlorobenzonitrile, m-chlorobenzonitrile, p-chlorobenzonitrile, 2,6-dichlorobenzonitrile, 3,5-dichlorobenzonitrile, 3,5-dichloro-2,4,6-trifluorobenzonitrile, 3-chloro-2,4,5,6-tetrafluorobenzonitrile, pentachlorobenzonitrile, 3-chlorophthalonitrile, 3,6-dichlorophthalonitrile, 4,5-dichlorophthalonitrile, tetrachlorophthalonitrile, 5-chloroisophthalonitrile, 5-chloro-2,4,6-trifluoroisophthalonitrile, tetrachloroisophthalonitrile, 1,2-dichloroterephthalonitrile, tetrachloroterephthalonitrile, 3-chloropyridine, 2,5-dichloropyridine, 2,3,5-trichloropyridine, 3,5-dichloro-2,4,6-trifluoropyridine, pentachloropyridine, 5-chloro-3-cyanopyridine, 6-chloro-3- cyanopyridine, 5-chloro-2,4,6-trifluoro-3-cyanopyridine, 2,4,5,6-tetrachloro-3-cyanopyridine, 6-chloro-4-cyanopyridine, 2,3,5,6-tetrachloro-4-cyanopyridine, 3,4,5,6-tetrachloro-2-cyanopyridine, and the compounds which are equivalent to the compounds mentioned above excepting they have bromine atoms in the place of chlorine atoms may be cited. Among the examples cited above, pentachlorobenzonitrile proves particularly preferable.

Generally, as the fluorinating agents for the halogen exchange reaction, such alkali metal fluorides as cesium fluoride, potassium fluoride, sodium fluoride, and lithium fluoride and such alkaline earth metal fluorides as calcium fluoride, barium fluoride, and magnesium fluoride are usable. Such transition metal fluorides as antimony fluoride are used occasionally. In this invention, all the fluorinating agents which are in popular use are invariably usable. Among other fluorinating agents mentioned above, alkali metal fluorides or alkaline earth metal fluorides which allow easy handling and permit ready commercial procurement are preferable, alkali metal fluorides are particularly preferable, and potassium fluoride is most preferable.

The fluorinating agent mentioned above must be in an amount at least equivalent to the amount of chlorine atoms or bromine atoms in the organic chloride or bromide compound, i.e. the starting raw material, to be substituted by the fluorine atoms. In the case of an alkali metal fluoride, this amount is preferable in the range of 1–2 mols based on the amount of chlorine atoms or bromine atoms.

In the production of the organic fluorine compound by the reaction of the organic chlorine or bromine compound with the fluorinating agent in benzonitrile as a solvent, the reaction is preferred to proceed under the spontaneously generated pressure. The reaction, when necessary, may be carried out particularly under a pressure which is further heightened with such an inert gas as, for example, nitrogen. Generally, the temperature is in the range of 190°–400° C. and the pressure in the approximate range of 0–30 kg/cm² (gauge pressure). Preferably, the temperature is in the range of 230–360° C. and the pressure in the approximate range of 1.5–22 kg/cm² (gauge pressure).

The duration of the reaction, though variable with the reaction temperature and the kind of starting raw material, is preferable in the approximate range of 2–48 hours.

The organic chlorine or bromine compound as the raw material may be preferablely added to the reaction system in an amount in the approximate range of 5–50 parts by weight, preferably 20–40 parts by weight, based on 100 parts by weight of benzonitrile as the solvent.

The halogenation exchange reaction mentioned above, when the reaction temperature is low and the duration of the reaction is short, has the possibility of partially forming a compound which has the chlorine atoms or bromine atoms thereof not completely exchanged. Where the compound aimed at by the reaction such as, for example, pentafluorobenzonitrile (boiling point 161° C. under 760 mmHg) or pentafluoropyridine (boiling point 84° C. under 760 mmHg) has a low boiling point as compared with the boiling point of benzonitrile as a solvent (191° C. under 760 mmHg), this compound can be extracted by stripping while a high boiling chlorine or bromine-containing fluorine compound is left behind as dissolved in the benzonitrile in the reaction kettle. By recovering the residual benzonitrile solution and reusing this solution as a solvent in the next round of the reaction, the chlorine or bromine-containing fluorine compound as the unaltered intermediate can be easily converted into the compound aimed at. By reusing the recovered benzonitrile solvent as described above, the yields of the compound aimed at such as, for example, pentafluorobenzonitrile or pentafluoropyridine can be heightened.

The halogen exchange reaction is preferred to be carried out under an anhydrous condition as far as circumstances permit for the purpose of repressing the formation of acid fluorides of an aromatic compound through a secondary reaction and heightening the reaction velocity as well. It is, therefore, preferable that the water be removed by distillation as an azeotrope with benzene or toluene prior to the reaction.

This invention prefers the halogen exchange reaction to proceed in the presence of an interphase transfer catalyst additionally incorporated in the reaction system. The presence of the interphase transfer catalyst is advantageous in respect that it heightens the reaction velocity and permits a decrease in the duration of the reaction. As the interphase transfer catalyst, such crown compounds as dibenzo-18-crown-6-ether and polyethylene glycols having molecular weights of 300–600 can be used. Adequately, the amount of the interphase transfer catalyst to be added is in the range of 0.01–0.25 mol, preferably 0.05–0.20 mol, per mol of the organic chlorine or bromine compound as the raw material.

The organic fluorine compound which is obtained by the halogen exchange reaction mentioned above is an organic fluorine compound which corresponds to the starting raw material compound. In the organic fluorine compounds, fluorinated aromatic compounds are preferred over the other compounds. Particularly, the fluorinated aromatic compounds represented by the following formula (8)

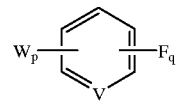

(8)

wherein V is N, CW, or CF, W is Cl, Br, CN, or NO$_2$, p is an integer of 0–4, q is an integer of 1–5, and the sum of p and q is an integer of 1–5, are preferable.

In the fluorinated aromatic compounds represented by the formula (8) mentioned above, the fluorinated aromatic compounds represented by the formula (9)

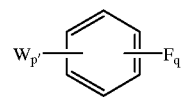

(9)

wherein W is Cl, Br, CN, or NO$_2$, p' is an integer of 0–5, q', is an integer of 1–6, and the sum of p' and q' is an integer of 1–6, or the formula (10)

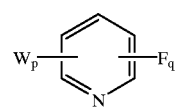

(10)

wherein W is Cl, Br, CN, or NO$_2$, p is an integer of 0–4, q is an integer of 1–5, and the sum of p and q is an integer of 1–5, are preferable.

Further, in the fluorinated aromatic compounds represented by the formula (9) mentioned above, the fluorinated aromatic compounds represented by the formula (11)

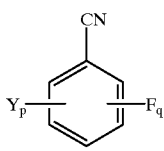

(11)

wherein Y is Cl or Br, p is an integer of 0–4, q is an integer of 1–5, and the sum of p and q is an integer of 1–5, or the formula (12)

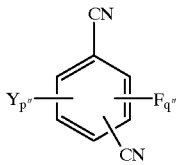

(12)

wherein Y is Cl or Br, p" is an integer of 0–3, q" is an integer of 1–4, and the sum of p" and q" is an integer of 1–4, are particularly preferable.

Further, in the fluorinated aromatic compounds represented by the formula (10) mentioned above, the fluorinated aromatic compounds represented by the formula (13)

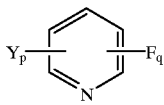

(13)

wherein Y is Cl or Br, p is an integer of 0–4, q is an integer of 1–5, and the sum of p and q is an integer of 1–5, or the formula (14)

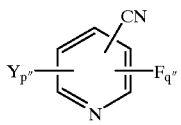

(14)

wherein Y is Cl or Br, p" is an integer of 0–3, q" is an integer of 1–4, and the sum of p" and q" is an integer of 1–4, are particularly preferable.

As typical examples of the fluorinated aromatic compound, fluorobenzene, polyfluorobenzenes, o-fluoronitrobenzene, m-fluoronitrobenzene, p-fluoronitrobenzene, 2,4-dinitrofluorobenzene, o-fluorobenzene nitrile, m-fluorobenzene nitrile, p-fluorobenzene nitrile, 2,6-difluorobenzonitrile, 3,5-difluorobenzonitrile, 3,5-difluoro-2,4,6-trichlorobenzonitrile, pentafluorobenzonitrile, 3-fluorophthalonitrile, 3,6-difluorophthalonitrile, 4,5-difluorophthalonitrile, tetrafluorophthalonitrile, 5-fluoroisophthalonitrile, 5-chloro-2,4,6-trifluoroisophthalonitrile, tetrafluoroisophthalonitrile, 1,2-difluoroterephthalonitrile, tetrafluoroterephthalonitrile, 3-fluoropyridine, 2,5-difluoropyridine, 2,3,5-trifluoropyridine, 3,5-difluoro-2,4,6-trifluoropyridine, pentafluoropyridine, 5-fluoro-3-cyanopyridine, 6-fluoro-3-cyanopyridine, 5-chloro-2,4,6-trifluoro-3-cyanopyridine, 6-fluoro-4-cyanopyridine, 2,3,5,6-tetrafluoro-4-cyanopyridine, and 3,4,5,6-tetrafluoro-2-cyanopyridine which are useful compounds as intermediates for the synthesis of agricultural chemicals, medicines, and dyes may be cited. Among other fluorinated aromatic compounds enumerated above, pentafluorobenzonitrile is particularly preferable.

The benzonitrile solvent which is used in the halogen exchange reaction mentioned above can be easily separated from the product of reaction by distillation and the recovered benzonitrile can be reused as the solvent.

Another method for the production of an organic fluorine compound as a means for accomplishing the objects of this invention is characterized by causing an organic chlorine or bromine compound to react with a fluorinating agent and then treating the reaction solution or the product of the reaction with an aqueous liquid thereby separating the water layer. By treating the reaction solution or the product of the treatment with the aqueous liquid thereby separating the water layer subsequently to the halogenation exchange reaction, the acid fluorides of an aromatic compound which exist in a minute amount in the reaction solution or the product of the reaction can be effectively removed.

Specifically, the acid fluorides of an aromatic compound which are contained in the reaction solution or the product of the reaction subsequently to the halogenation exchange reaction, when boiled with water, are hydrolyzed and consequently converted into such aromatic compounds as benzoic acid and hydrofluoric acid. The aromatic compounds such as benzoic acid which are the products of decomposition are sparingly soluble in cold water and readily soluble in hot water. The liquid resulting from the boiling treatment, therefore, is divided into an organic layer containing an organic fluorine compound, the product of the reaction, and a water layer containing such products of decomposition as acid fluorides of an aromatic compound. The acid fluorides of the aromatic compound, therefore, can be removed from the liquid by separating and removing the water layer while the liquid is still in a state of high temperature.

Similarly, the acid fluorides of the aromatic compound are hydrolyzed and separated into the water layer side when they are combined with an acidic aqueous liquid and then left standing in the presence of an acidic substance. In this case, the hydrolysis can be attained at a lower temperature in a shorter span of time by using the acidic aqueous liquid in a higher concentration (as evinced by the fact that for the purpose of thorough hydrolysis, 15 hours' treatment suffices at 50° C. in the presence of 40% sulfuric acid and 3 hours' treatment suffices at normal room temperature in the presence of 70% sulfuric acid where 24 hours' treatment is required at 70° C. in the sole presence of water, for example). Thus, the acid fluorides of the aromatic compound can be selectively separated and removed.

The aqueous liquids which can be effectively added to the reaction solution or the product of the reaction mentioned above are water and acidic aqueous liquids. The acidic aqueous liquids are preferred to water. As typical examples of the acidic aqueous liquid, the aqueous solutions of such inorganic acids as, for example, sulfuric acid, hydrochloric acid, and nitric acid may be cited. Among the aqueous solutions mentioned above, the aqueous solution of sulfuric acid are particularly preferable.

As respects the concentration of the acidic aqueous solution, where the aqueous sulfuric acid solution is used, the content of sulfuric acid is preferred to be 5–80%, particularly 15–70%. When the acidic aqueous solution is used in a high concentration, the temperature of treatment can be lowered and the duration of treatment can be decreased. When it is used in a low concentration, the hydrolysis of the reaction product itself can be repressed.

Incidentally, the temperature of treatment is suitably decided to suit the kind of the aqueous liquid to be used and the concentration of the aqueous liquid. When the acidic aqueous liquid is used, it is at least necessary for the treatment to be carried out at a temperature such that the product aimed at may not be hydrolyzed by the acidic aqueous liquid. Otherwise, the product aimed at is hydrolyzed, and rendered readily soluble in water, and consequently solved into the water layer side during the course of this treatment and the solved portion is separated and removed from the product of the reaction and ultimately suffered to result in lowering the yields. Thus, the treatment is preferred to be carried out at a temperature in the range of 5°–130° C., particularly 10°–80° C.

The amount of the aqueous liquid to be added to the reaction solution or the product of the reaction, in consideration of the effectiveness of the contact between the water layer and the organic layer, the efficiency of the hydrolysis of the acid fluorides, and the ease with which the water layer and the organic layer are separated, is in the range of 30–600 parts by weight, preferably 50–300 parts by weight, based on 100 parts by weight of the organic fluorine compound in the reaction solution or the product of the reaction. The organic fluorine compound which is the product aimed at (the intermediate for synthesis) is hydrolyzed by being further boiled in an acidic aqueous iquid and can be used as the final product, one kind of a compound useful for agricultural chemicals, medicines, and dyes, or as an intermediate for specific synthesis. When the acid fluorides of an aromatic compound are present in this process of production, the acid fluorides of the aromatic compound are likewise hydrolyzed and consequently suffered to form hydrofluoric acid (fluorine ions) which is a corrosive substance and corrode the reaction device (facilities). Thus, the acid fluorides of the aromatic compound must be removed prior to the step of production mentioned above. As the acidic aqueous liquid, the waste aqueous solution which occurs after the completion of the next step (the step of hydrolysis) can be used in its unmodified form. The substance aimed at which remains in the waste acid can be recycled in its unmodified form and utilized effectively.

The term "reaction product" as used herein refers to the organic fluorine compound, i.e. the product aimed at which is obtained by separating and refining by such well-known means as distillation the reaction solution resulting from the reaction of an organic chlorine or bromine compound with a fluorinating agent without resorting to the means for removal of acid fluorides of the aromatic compound contemplated by this invention. The term "reaction product" as used herein, therefore, embraces the acid fluorides of the aromatic compound.

Next, the method for the production of pentafluorobenzoic acid according to the present invention is characterized by (1) causing pentachlorobenzonitrile to react with a fluorinating agent in benzonitrile as a solvent thereby obtaining pentafluorobenzonitrile, (2) hydrolyzing the benzoic acid fluoride present in the resultant reaction solution by the use of an acidic aqueous liquid thereby separating the hydrolyzate into the water layer side, and subsequently (3) hydrolyzing the treated pentafluorobenzonitrile in an aqueous sulfuric acid solution thereby producing pentafluorobenzoic acid.

The method for the production of the pentafluorobenzoic acid mentioned above may well be called a preferred embodiment of the method for the production of the organic fluorine compound described above. As a means for preventing the occurrence of acid fluorides of an aromatic compound, therefore, the halogen exchange reaction may be carried out, as occasion demands, in the presence of the oxide, hydroxide, and/or carbonate of an alkali metal or an alkaline earth metal.

The reaction of hydrolysis of pentafluorobenzonitrile in an aqueous sulfuric acid solution is preferred to be carried out under normal pressure. It may be optionally performed in a pressure vessel under the spontaneously generated pressure. This reaction is adequately carried out at a temperature generally in the range of 100–200° C., preferably in the range of 130–170° C. Though the duration of the reaction varies with the temperature of the reaction and the concentration of sulfuric acid, it falls generally in the range of 3–48 hours, preferably in the range of 5–24 hours. The sulfuric acid concentration falls generally in the range of 40–85%, preferably in the range of 55–75%.

The pentafluorobenzoic acid which is obtained after the completion of the reaction exhibits low solubility in the aqueous sulfuric acid solution at normal room temperature. Generally, it can be separated from the aqueous sulfuric acid solution by being cooled and then filtered.

Since the cakes separated by the filtration contain sulfuric acid and ammonium sulfate, they are preferred to be washed with water. The washings consequently obtained may be recycled to the reaction solution because they contain pentafluorobenzoic acid dissolved therein. It may be otherwise used as the washing liquid for the next lot. The recycling thus carried out can prevent the possible decline of the yields of pentafluorobenzoic acid and decrease the amount of waste water as well.

The method of hydrolysis with sulfuric acid and the method of treatment described above can be similarly applied to the hydrolysis of 3,4,5,6-tetrafluorophthalonitrile, for example.

Now, the method for the production of pentafluorobenzoic acid will be described below by reference to the accompanying drawings.

FIG. 1 is a schematic diagram illustrating one preferred embodiment of the production device to be used for the method of production of pentafluorobenzoic acid according to the present invention. As illustrated in FIG. 1, the method of this invention for the production of pentafluorobenzoic acid supplies the starting raw materials, i.e. pentachlorobenzonitrile (PCBN), benzonitrile (BN) solvent, and a fluorinating agent (KF), and, when necessary for the purpose of preventing the occurrence of acid fluorides of an aromatic compound, further supplies the oxide, hydroxide, and/or carbonate (KOH) of an alkali metal or an alkaline earth metal via various pipes 11–14 to a halogenation exchange reaction device 15. Inside the reaction device 15, the pentachlorobenzonitrile reacts with the fluorinating agent in the benzonitrile solvent to give rise to pentafluorobenzonitrile. The details of the process of this reaction have been already described above with respect to the method for the production of an organic fluorine compound. Particularly this invention prefers the reaction to proceed in the presence of the oxide, hydroxide, and/or carbonate of an alkali metal or an alkaline earth metal from the viewpoint of preventing the occurrence of acid fluorides of an aromatic compound. This measure can prevent the reaction device from corrosion during the course of the halogenation exchange reaction.

The reaction solution consequently obtained is transferred via a pipe 16 to an evaporation device 17. In the evaporation device 17, the reaction solution is deprived of relatively easily separable potassium chloride (KCl) by crude distillation, with the unaltered fluorinating agent (KF) left behind as a residue. The residue is removed via a pipe 18. By this process removing potassium chloride (KCl) from the reaction solution and allowing the unaltered fluorinating agent (KF) to remain as the residue, it is made possible for the high boiling component separated at the next step of distillation to be recovered and reused as the benzonitrile solvent.

Then, the separated liquid resulting from the removal of the residue from the reaction solution is transferred via a pipe 19 to a precision fractional distillation device 20. In the precision fractional distillation device 20, such high boiling chlorine-containing fluorine compounds as 3,5-dichloro-2,4,6-trifluorobenzonitrile and 3-chloro-2,4,5,6-tetrafluorobenzonitrile whose chlorine atoms have not been completely exchanged by the work of distillation remain as solved in the benzonitrile solvent. The residual high boiling components are circulated through a pipe 21 and are reused as the recovered benzonitrile solvent. As a result, the chlorine-containing fluorine compounds remaining as unaltered intermediates can be easily converted into pentafluorobenzonitrile (PFBN), the compound aimed at, with the result that the yields of the compound aimed at will be heightened.

The low boiling component (more volatile component) of pentafluorobenzonitrile containing benzoic acid fluoride is transferred via a pipe 22 to an acid fluoride treating device 23. In the acid fluoride treating device 23, the benzoic acid fluoride present in the low boiling component is exclusively hydrolyzed by the use of an acidic aqueous liquid (containing ammonium sulfate, PFBN, and PFBA when the waste sulfuric acid resulting from the hydrolysis at the next step is used) supplied via a pipe 24 and the hydrolyzate is separated in the water layer side. After this treatment, the water layer containing benzoic acid and hydrofluoric acid which are decomposed components of the benzoic acid fluoride is separated and removed via a pipe 25. Since the benzoic acid fluoride is removed by the present operation which constitutes itself one of the characteristic features of this invention, the occurrence of fluorine ions, a corrosive substance, originating in the benzoic acid fluoride can be prevented during the hydrolysis of pentafluorobenzonitrile at the next step.

The pentafluorobenzonitrile resulting from the treatment and extracted as an organic layer is transferred via a pipe 26 to a hydrolyzing device 27. In the hydrolyzing device 27, the pentafluorobenzonitrile is hydrolyzed in an aqueous sulfuric acid solution ($H_2SO_4$ aq) supplied via a pipe 28 so as to produce pentafluorobenzoic acid.

The solution resulting from the treatment is transferred via a pipe 29 to a filtration washing part 30. In the filtration washing part 30, the solution is filtered and the cakes separated by the filtration are thoroughly washed with washing water ($H_2O$) supplied through a pipe 34 and transferred via a pipe 31 to a drying part 32. In the drying part 32, the thoroughly cleaned cakes are dried to obtain pentafluorobenzoic acid (PFBA) wished to be produced. Then, the waste sulfuric acid (containing PFBN and PFBA) of the filtrate is supplied via the pipe 24 to the acid fluoride treating device 23 and optionally reused as an acidic aqueous liquid. The washings resulting from the washing of the cakes of filtration are transferred from a pipe 33 via the pipe 28 to the hydrolyzing device 27 and optionally recycled to the reaction solution. The saturated aqueous solution of PFBA is forwarded via a pipe 35 and optionally transferred via a pipe 34 to be reused as the washing liquid for the next lot. Part of the saturated aqueous solution is discharged as a waste via a pipe 36. The method for the production of pentafluorobenzoic acid thus constructed can be similarly applied to the process which comprises causing a phthalonitrile compound such as, for example, 3,4,5,6-tetrachlorophthalonitrile, to react with a fluorinating agent in the benzonitrile solvent thereby forming tetrafluorophthalonitrile and then hydrolyzing 3,4,5,6-tetrafluorophthalonitrile with an aqueous sulfuric acid solution thereby producing 3,4,5,6-tetrafluorophthalic acid.

EXAMPLE 1

In an autoclave provided with a stainless steel (SUS 316) reaction vessel, 500 cc in inner volume, 190 g of benzonitrile, 66.1 g (0.24 mol) of pentachlorobenzonitrile, 83.7 g (1.44 mols) of dry potassium fluoride in the form of fine powder, and 0.084 g of potassium hydroxide were placed and, after the air entrapped in the reaction vessel was displaced with nitrogen gas, heated and stirred at 315° C. for 18 hours. After the reaction was completed, the reaction solution was treated with a rotary evaporator under the final conditions of 200° C. of external temperature and 20 Torrs of vacuum degree to separate potassium chloride and the unaltered potassium fluoride therefrom.

The liquid consequently separated was treated with a precision fractional distillation device to recover 33.3 g of pentafluorobenzonitrile (fraction of 161–162° C. under normal pressure) as the product aimed at. When the recovered pentafluorobenzonitrile was analyzed by gas chromatography, it was found to contain 0.039 g of benzoic acid fluoride (1170 ppm based on the amount of pentafluorobenzonitrile). After the operation, the stainless steel reaction vessel showed no discernible sign of corrosion.

Control 1

A reaction was performed and the reaction product was treated by following the procedure of Example 1 while omitting the addition of potassium hydroxide. As a result, 35.9 g of pentafluorobenzonitrile (fraction of 161°–162° C. under normal pressure) was recovered as the product aimed at. When the recovered pentafluorobenzonitrile was analyzed by gas chromatography, it was found to contain 0.21 g of benzoic acid fluoride (5850 ppm based on the amount of pentafluorobenzo-nitrile). The stainless steel reaction vessel showed a sign of slight corrosion.

EXAMPLE 2

At normal room temperature, 30 g of the pentafluorobenzonitrile obtained in Example 1 and 20 g of an aqueous 70% sulfuric acid solution added thereto were stirred together for 3 hours. Then, the resultant mixture was left standing at rest and allowed to separate into an organic layer (pentafluorobenzonitrile layer) and a water layer. When the organic layer was analyzed, it was found to contain absolutely no benzoic acid fluoride.

EXAMPLE 3

Thirty (30) g of pentafluorobenzonitrile (containing 1400 ppm of benzoic acid fluoride) obtained in the same manner as in Example 1 and 60 g of an aqueous 50% sulfuric acid solution added thereto were stirred together at 40° C. for 23 hours. Then, the resultant mixture was left standing at rest and allowed to separate into an organic layer (pentafluorobenzonitrile layer) and a water layer. When the organic layer was analyzed, it was found to have the benzoic acid fluoride content decreased to 0.0046 g (153 ppm based on the amount of pentafluorobenzonitrile).

EXAMPLE 4

Thirty (30) g of pentafluorobenzonitrile (containing 1210 ppm of benzoic acid fluoride) obtained in the same manner as in Example 1 and 60 g of an aqueous 20% sulfuric acid solution added thereto were stirred together at 50° C. for 24 hours. Then, the resultant mixture was left standing at rest and allowed to separate into an organic layer (pentafluorobenzonitrile layer) and a water layer. When the organic layer was analyzed, it was found to contain absolutely no benzoic acid fluoride.

EXAMPLE 5

Thirty (30) g of pentafluorobenzonitrile (containing 950 ppm of benzoic acid fluoride) obtained in the same manner as in Example 1 and 60 g of water added thereto were stirred together at 70° C. for 24 hours. Then, the resultant mixture as left standing at rest and allowed to separate into an organic layer (pentafluorobenzonitrile layer) and a water layer. When the organic layer was analyzed, it was found to contain absolutely no benzoic acid fluoride.

EXAMPLE 6

In a glass flask, 300 cc in inner volume, 26.5 g of pentafluorobenzonitrile obtained by the treatment of Example 4 and an aqueous sulfuric acid solution prepared with 35.0 g of concentrated sulfuric acid and 36.5 g of water were placed and left reacting at a temperature in the range of 145°–165° C. for 15 hours. Then, the resultant reaction solution was filtered. The cakes separated consequently were thoroughly cleaned with a washing liquid saturated with pentafluorobenzoic acid and then dried. As a result, 29.1 g of pentafluorobenzoic acid was obtained. When the glass flask after the use in the reaction was visually examined, it showed no sign of either loss of transparency or corrosion of glass.

Control 2

A reaction was performed and the product of reaction was treated by following the procedure of Example 6 while using the pentafluorobenzonitrile (containing 1150 ppm of benzoic acid fluoride) obtained by the method of Example 1 instead. When the glass flask used in the reaction was visually examined, it showed a sign of loss of transparency throughout the entire flask and a clear sign of corrosion of glass.

EXAMPLE 7

Thirty (30) g of the pentafluorobenzonitrile (containing 1400 ppm of benzoic acid fluoride) obtained by the method of Example 1 and 60 g of an aqueous waste sulfuric acid solution (containing 27.6 wt. % of $H_2SO_4$, 5.3 wt. % of $(NH_4)SO_4$, and 0.7 wt. % of pentafluorobenzoic acid) of Example 6 added thereto were stirred together at 50° C. for 24 hours. Then, the resultant mixture was left standing at rest and allowed to separate into an organic layer (pentafluorobenzonitrile layer) and a water layer. When the organic layer was analyzed, it was found to contain absolutely no detectable benzoic acid fluoride.

EXAMPLE 8

A reaction was performed at 270° C. for 16 hours by following the procedure of Example 1 while using 80.0 g (0.301 mol) of 3,4,5,6-tetrachlorophthalonitrile in the place of pentachlorobenzonitrile and 0.1 g of sodium hydroxide in the place of potassium hydroxide. After the reaction was completed, the reaction solution was cooled to room temperature and then filtered to remove the suspended potassium chloride and the unaltered potassium fluoride. When the benzonitrile solution as the mother liquor was analyzed by gas chromatography, it was found to contain 55.4 g of 3,4,5,6-tetrafluorophthalonitrile and 0.018 g of benzoic acid fluoride (325 ppm based on the amount of 3,4,5,6-tetrafluorophthalonitrile). The stainless steel reaction vessel showed no discernible sign of corrosion.

Control 3

A reaction was performed and the reaction product was treated by following the procedure of Example 1 while omitting the addition of sodium hydroxide. When the benzonitrile solution as the mother liquor was similarly analyzed, it was found to contain 0.200 g of benzoic acid fluoride (3600 ppm based on the amount of 3,4,5,6-tetrafluorophthalonitrile). The stainless steel reaction vessel showed a sign of slight corrosion.

EXAMPLE 9

One hundred (100) g of the benzonitrile solution as the mother liquor obtained in Example 8 and 80 g of an aqueous 70% sulfuric acid solution added thereto were stirred together at room temperature for 2 hours. Then, the resultant reaction solution was left standing at rest and allowed to separate into an organic layer (benzonitrile solution layer) and a water layer. When the organic layer was analyzed, it was found to contain absolutely no benzoic acid fluoride.

The entire disclosure of Japanese Patent Application No. 9-229615 filed on Aug. 26, 1997 including specification, claims and summary are incorporated herein by reference in its entirety.

What is claimed is:

1. A method for the production of an organic fluorine compound which comprises reacting an organic chlorine or bromine compound with a fluorinating agent in benzonitrile as a solvent in the presence of the oxide, hydroxide, and/or carbonate of an alkali metal or an alkaline earth metal under preventing formation of acid fluorides of an aromatic compound or removing said acid fluorides formed.

2. A method according to claim 1, wherein said organic chlorine or bromine compound is a chloride or bromide of an aromatic compound.

3. A method according to claim 1, wherein said fluorinating agent is at least one member selected from the group consisting of fluorides of alkali metals and alkaline earth metals.

4. A method according to claim 1, wherein said acid fluoride of an aromatic compound is benzoic acid fluoride.

5. A method according to claim 1, wherein said organic chlorine or bromine compound is pentachlorobenzonitrile and said organic fluorine compound is pentafluorobenzonitrile.

6. A method for the production of an organic fluorine compound which comprises causing an organic chlorine or bromine compound to react with a fluorinating agent in benzonitrile as a solvent, treating the reaction solution or the reaction product with an aqueous liquid, and then effecting separation of a water layer thereby removing acid fluorides of an aromatic compound.

7. A method according to claim 6, wherein said aqueous liquid is an acidic aqueous liquid.

8. A method according to claim 6, wherein the reaction is carried out in the presence of oxide, hydroxide, and/or carbonate of an alkali metal or alkaline earth metal.

9. A method according to claim 6, wherein said organic chlorine or bromine compound is a chloride or bromide of an aromatic compound.

10. A method according to claim 6, wherein said fluorinating agent is at least one member selected from the group consisting of fluorides of alkali metals and alkaline earth metals.

11. A method according to claim 8, wherein said acid fluoride of an aromatic compound is benzoic acid fluoride.

12. A method according to claim 6, wherein said organic chlorine or bromine compound is pentachlorobenzonitrile and said organic fluorine compound is pentafluorobenzonitrile.

13. A method for the production of pentafluorobenzoic acid which comprises causing pentachlorobenzonitrile to react with a fluorinating agent in benzonitrile as a solvent thereby forming pentafluorobenzonitrile, hydrolyzing the benzoic acid fluoride present in the resultant reaction solution with an acidic aqueous liquid and separating the resultant hydrolyzate into a water layer side, and hydrolyzing the pentafluorobenzonitrile resulting from the treatment in an aqueous sulfuric acid solution thereby obtaining pentafluorobenzoic acid.

14. A method according to claim 1, wherein an amount of the oxides, hydroxides or carbonates of the alkali metal or the alkaline earth metal is between about 50 to about 1500 ppm to benzonitrile.

15. The method according to claim 14, wherein the amount of the alkali metal or the alkaline earth metal is between about 100 to 600 ppm to benzonitrile.

16. The method according to claim 1, wherein an amount of acid fluoride is less than about 2000 ppm to the organic fluoride compound.

17. The method according to claim 14, wherein an amount of acid fluoride is less than about 2000 ppm to the organic fluoride compound.

* * * * *